US006333055B1

(12) United States Patent
Wiklund

(10) Patent No.: US 6,333,055 B1
(45) Date of Patent: Dec. 25, 2001

(54) USE OF AMMONIUM COMPOUNDS AND/OR UREA

(76) Inventor: Lars Wiklund, Sveavägen 2, S-752, 36 Uppsala (SE)

( * ) Notice: Subject to any disclaimer, the term of this patent is extended or adjusted under 35 U.S.C. 154(b) by 0 days.

(21) Appl. No.: 09/142,145

(22) PCT Filed: Mar. 4, 1997

(86) PCT No.: PCT/SE97/00361

§ 371 Date: Sep. 2, 1998

§ 102(e) Date: Sep. 2, 1998

(87) PCT Pub. No.: WO97/34590

PCT Pub. Date: Sep. 25, 1997

(30) Foreign Application Priority Data

Mar. 20, 1996 (SE) .................................................. 9601057

(51) Int. Cl.$^7$ .......................... A61K 33/02; A61K 31/04; A61K 31/17; A61K 47/00
(52) U.S. Cl. .......................... 424/720; 424/439; 424/719; 426/801; 514/588; 514/740
(58) Field of Search .................................. 424/93.1, 93.4, 424/720, 719, 439; 514/663, 664, 588, 740; 426/580, 582, 583, 586, 587, 588, 625, 628

(56) References Cited

U.S. PATENT DOCUMENTS

| 4,668,772 | * | 5/1987 | Lee ......................................... 530/407 |
| 4,849,241 | * | 7/1989 | Al-Mashiki et al. ................. 426/583 |
| 5,169,666 | * | 12/1992 | Woychik ............................... 426/580 |
| 5,312,839 |   | 5/1994 | Nakada .................................. 514/634 |

FOREIGN PATENT DOCUMENTS

96/11014    4/1996   (WO) .

OTHER PUBLICATIONS

WEST online, file DWPI, Acc. No. 1984–189375, Drescher et al., DD 208542 A (1984), Abstract.*
Pattison et al., Proposed link between *Heliobacter pylori* and sudden infant death syndrome, Medical Hypotheses, pp. 365–369, 1997.*
Smith, Feeding Overstrength Cows' Milk to Babies, British Medical Journal, pp. 741–742, Dec. 1974.*
Blumenfeld et al., Postmortem Vitreous Humor Chemistry in Sudden Infant Death Syndrome and in Other Causes of Death in Childhood, American Journal of Clinical Pathology, pp. 219–223, Feb. 1979.*
George et al., Faecal Microflora and Urease Activity during the First Six Months of Infancy, Upsala Journal of Medicine, vol. 101, No. 3, pp. 233–250, 1996.*
Darling et al., Utilization of non–protein nitrogen in whey –dominant formulae by low–birthweight infants, Clinical Science, pp. 543–548, 1993.*
"CRC Handbook of Food Additives", by Thomas E. Furia, Second Edition, CRC Press, Inc., 1977, vol. I, p. 623.
"CRC Handbook of Food Additives", by Thomas E. Furia, Second Edition, CRC Press, Inc., 1977, vol. II, p. 258.

* cited by examiner

*Primary Examiner*—John Pak
*Assistant Examiner*—Frank Choi
(74) *Attorney, Agent, or Firm*—McDermott, Will & Emery

(57) ABSTRACT

The use of a physiologically innocuous ammonium compound and/or urea as an additive to an infant formula or a pap or for the preparation of a pharmaceutical composition for the prophylaxis of sudden infant death syndrome (SIDS) is disclosed as is also an infant formula or a pap which in addition to conventional ingredients contains a physiologically innocuous ammonium compound and/or urea. Futhermore, a method of preventing SIDS is disclosed, which method comprises administering to the infant an infant formula or a pap as indicated above, and a method for the prophylaxis of SIDS, wherein a pharmaceutical composition containing a physiologically innocuous ammonium compound and/or urea is administered to the infant or the appropriately selected or modified non-pathogenic, urease-producing bacteria are supplied to the gastrointestinal tract of the infant. Finally a method for the diagnosis of the risks for SIDS is disclosed according to which method the faeces of the infant are analyzed with respect to the presence of urea, urease activity and/or ammonium ions, the presence of urea, the absence or abnormally low urease activity and ammonium ion, respectively, indicating risks for SIDS.

11 Claims, No Drawings

USE OF AMMONIUM COMPOUNDS AND/OR UREA

This application is a 371 of PCT/SE97/00361, filed on Mar. 4, 1997.

The present invention relates to the new use of physiologically innocuous ammonium compounds and/or urea, an infant formula or a pap and a method for the prevention or prophylaxis of cot death.

The phenomenom called "cot death" or "Sudden Infant Death Syndrome" (SIDS) has heretofore not been given any satisfactory explanation.

The syndrome affects apparently previously healthy children at the age of about 3 to 5 months, which in most cases are found dead under sleep by their parents. As far as I know hardly any cases of SIDS have been reported, wherein death has suddenly occurred in a child which has been regarded as awake. On the contrary a general pattern seems to be that the child has fallen asleep and is sleeping very peacefully after having been normally awake and in certain cases even having been sensorically comparatively well stimulated before falling asleep. Any signs of hypoxia (cyanosis) have as a rule never been observed before death. In certain cases, however, it has been asserted that autopsy findings have shown signs of chronical hypoxia [Hunt C E, Clin Perinatol, 19, 757–771 (1992)]. Furthermore, it has sometimes been asserted that insufficient breathing has been observed clinically on some children and sometimes also on brothers and sisters to children which have died from SIDS. Lately parents to children at an age of less than 6 months have been recommended to have the child sleeping on its back because it has appeared that this recommendation, when complied with, has resulted in a lower incidence of SIDS. Recently results have been published which indicate that supine position in the bed should be the position in which a high ambient temperature is best tolerated. [Ponsonby A-L et al, N Engl J Med, 329, 377–382 (1993)].

The present invention emanates from a new hypothesis about the cause of SIDS based on certain observations made and earlier published theories for the metabolism of mammals.

In order that an animal or a human being should be able to live it is required that its body functions are regulated in such a way that there is an acid-base balance. Expressed in another way: A normal pH-value must exist in the cells, in the extracellular liquid and in the cell organelles. If this is not the case first slight functional disorders, then even increasing diseases and finally death of structures, cells and the whole organism occurs. For instance, it is known that the mortality in several diseases increases when the pH value of the extracellular liquid (normally 7.40) is above 7.55 or below 7.20.

Under the latest decades the opinion of the acid-base balance has not changed materially. During the 1980's, however, Atkinson and co-workers [Atkinson D E et al, Curr Top Cell Regul, 21, 261–302 (1982)] again called attention to the previously known, but among physiologists and medical physicians not accepted fact that the metabolism of mammals not only produced the main metabolites carbon dioxide, water and urea but also hydrogen carbonate. His theory also meant that the metabolism by producing hydrogen carbonate above all via amino acid metabolism in order to result in the metabolic end products carbon dioxide and water must be supplied with protons and that this process for quantitative reasons had to occur via the ornithine cycle. One of the objections against this theory has been that if such an important life process does not function the animal or the human being in question should rapidly die. However, no such lacking function of the system proposed by Atkinson has ever been pointed out and even less been proven which constitutes one of the deficiencies of his theory.

The hypothesis that the above-mentioned acid-base system at a possible malfunction might cause the part of SIDS which can be explained with a respiratory insufficiency has now been made the basis of the present invention.

The fundamental principle of the hypothesis above is that deficient protonizing of endogenously produced hydrogen carbonate rapidly, according to Atkinson, results in a progressive alkalizing which as known about this condition may lead to progressive hypoventilation, i.e. insufficient breathing. An increase in the concentration of hydrogen carbonate is certainly counteracted by a compensatory increase in $PCO_2$ which is one of the physiological results of a hypoventilation.

The other consequence of the hypoventilation is one of a relative hypoxemia (not particularly pronounced low arterial oxygen gas saturation of haemoglobin due to a normally left-displaced saturation curve for oxygen in small children) and later a secondary lactic acidosis (lactic acid acidosis). This will thus in combination lead to a raise in the pH-value to a metabolic alkalosis which finally only partially is compensated by a hypercapnia just as the lactic acid acidosis already mentioned. The cumulation of hydrogen carbonate and the alkalosis caused thereby hence dominates this process. The metabolic alkalosis which hence is only partially compensated, enhances still more the Hb dissociation curve for fetal haemoglobin which is already displaced to the left. Added to this effect upon the $O_2$ dissociation curve will be the influence that a possible increase in body temperature exerts on $PCO_2$, which accordingly increases and as a consequence thereof contributes to a progressive respiratory depression. The result will be an increasing and finally massive metabolic alkalosis which leads to further respiratory depression, hypercapnia and hypoxia, particularly in peripheral tissues, in spite of a relatively good arterial oxygen gas saturation and accordingly absence of cyanosis. Finally, the respiratory centre cannot function normally due to the progressive acid-base displacement and the hypoxia but during sleep, which often is combined with a child which is too warm (a high temperature increases $PCO_2$), a still more serious hypoxia appears as a consequence of the fact that the hypoxic respiration drive does not function in such small children. The end result will be a death which by physicians is given the diagnosis SIDS.

The deficient protonization of the hydrogen carbonate ions of the child might be an effect of a deficient supply of ammonium ions in the liver which in turn might be due to the lack of natural content of urea in the infant formulas or to the fact that the rich supply of urea in the mother's milk (often twice as much as in the mother's plasma) is not metabolized in the normal way to ammonium ions. This decomposition of urea usually occurs in the gastrointestinal tract by urease-producing bacteria which gradually colonize the initially sterile intestine of the neonate. The bacterial colonization normally occurs during the first weeks of life but might according to the present hypothesis have been delayed, inhibited, or be insufficient in another way in the children which experience a respiratory insufficiency resulting in SIDS.

It is thus well-known that the breast milk contains considerable amounts of urea. It is also known that the content of nitrogen not bound by proteins in breast milk is considerably higher than that corresponding to its content of urea. It has also been shown that this urea to some extent (about 20%) can be utilized as a substrate for the formation of alpha-aminonitrogen compounds, i.e. amino acids and proteins. Häussinger and co-workers [Häussihger D, Meijer A J, Gerok W, Sies H; "Hepatic nitrogen metabolism and acid-base homeostasis" in "pH homeostasis, mechanisms and control", Ed D Häussihger, Academic Press Ltd, London (1988), pp 337–377] have by experiments shown that the ammonium nitrogen from the portal area, especially at acidosis, can be utilized for synthesis of glutamine in the liver. It is also known by intensive care physicians that ammonium chloride supplied intravenously and perorally lowers base excess values and such supply is accordingly used as a matter of routine for the treatment of a metabolic alkalosis. When the patient treated is breathing by himself, the supply of ammonium will bring about a so-called compensatory hyperventilation. The present inventor has administered himself 80 mmoles ammonium chloride perorally and thereby has been able to establish that this substance obviously is resorbed very quickly from the gastrointestinal tract and causes a slight hyperventilation which in turn causes an increase in RQ ("Respiratory Quotient"=the quotient between the carbon dioxide emission and the oxygen gas uptake in a person—in both cases expressed in ml/min) from a value at rest of 0.82 to 0.87 and the elimination of carbon dioxide increases by 30 ml/min and that this seems to proceed for nearly 1 h, which corresponds to about 80 mmoles of carbon dioxide. Furthermore, there is a report on the concentration of urea in the vitreous body of dead SIDS patients which is compared to autopsy material from children deceased from other causes at the same age [Blumenfeld T A, et al, Am J Clin Pathol, 71, 219–223 (1979)]. It appeared that children deceased from SIDS have lower urea values than children deceased from other causes. As a normal enterohepatic circulation of urea and ammonium ion hypothetically does not function in these cases this should have the consequence that the production of urea is less than normally and since the volume of distribution is equal this means that the concentration in various body fluids decreases. The low concentration of urea found is thus not inconsistent with the hypothesis put forward here.

In certain autopsy materials from SIDS victims signs of chronical hypoxia have been observed as already mentioned above. On the other hand, nobody seems to have reported that children, which later have deceased in SIDS, before death had any clinical signs of hypoxemia in the form of cyanosis. These findings are well consistent with the fact that an oxygen gas dissociation curve displaced to the left more easily gives well oxygen gas saturated haemoglobin but that this also to a high degree renders the utilization of oxygen gas in the periphery more difficult and in extreme situations even might result in a tissue hypoxia there. The alkalosis is indeed partly counteracted by a lactic acidosis but it may be expected that also this compensating mechanism like the renal excretion of hydrogen carbonate finally appears insufficient. It should be remembered that the great endogenous production of hydrogen carbonate according to Atkinson is so great that absence of normal protonizing for only one day or a few days would result in a life-threatening alkalosis.

The cited finding that children which have died in SIDS have a low concentration of urea in the vitreous body of the eye probably indicates that this group of children forms less amounts of urea in their liver relative to other children. This might in turn indicate that either the bacterial formation of ammonium ion from urea in the intestine is defect and/or that the protein catabolism of the SIDS victims is less than in other children. The fact that colostrum contains considerably less urea than the breast milk some weeks later, however, indicates that there is an adaption between the neonate and the composition of the breast milk. In view of the fact that the amount of breast milk taken in increases gradually also the daily intake of urea increases. Nothing seems heretofore to have been published about the intake of ammonium ion nor about the amount of ammonium ion produced in the intestine and how this varies with the age of the child.

However, it is known that the urinary excretion per 24 hours of ammonium ion is reduced considerably in the course of the first six weeks of life at the same time as the urinary excretion of urea increases. A slowly increasing pH and base excess in the capillary blood of the child during the first six weeks of life has also been observed. Thus it is probable that the breast milk of the newly delivered mother also contains ammonia/ammonium ions. This will in such a case constitute a protection against a progressive alkalosis. A pilot study of three cases, performed by the present inventor, shows that early (2–4 weeks) breast milk contains 400–500 $\mu$mol/l of ammonia/ammonium ion and 5–6 mmol/l of urea. The ammonium ion content has been reduced to 25–75 $\mu$mol/l after 4 to 5 months.

On basis of the hypothesis stated above, the present invention relates according to one aspect thereof to the use of a physiologically innocuous ammonium compound and/or urea as an additive to an infant formula or a pap or for the preparation of a pharmaceutical composition for prophylaxis of SIDS.

According to another aspect of the invention there is provided an infant formula or a pap which is characterized in that it in addition to conventional constituents comprises a physiologically innocuous ammonium compound and/or urea in a physiologically innocuous and for the prevention of SIDS effective concentration.

According to another aspect of the invention there is provided a method of preventing SIDS, which method comprises administering to the infant an infant formula or a pap which has been added with a physiologically innocuous ammonium compound and/or urea in a physiologically innocuous and for the prevention of SIDS effective concentration.

According to a further aspect of the invention there is provided a method for the prophylaxis of SIDS, which method comprises administering to the infant a pharmaceutical composition containing a physiologically innocuous ammonium compound and/or urea in a physiologically innocuous and for the prophylaxis of SIDS effective concentration.

According to still another aspect of the invention there is provided a method for the prophylaxis of SIDS, which method comprises administering to the gastrointestinal tract of the infant appropriately selected and/or modified non-pathogenic, urease-producing bacteria.

According to a further aspect of the invention there is provided a method for the diagnosis of the risks for SIDS in an infant, which method comprises analysing the faeces of the infant with respect to the presence of urea, urease activity, and/or ammonium ions, the presence of abnormally high intact urea concentration, the absence of or abnormally low urease activity and ammonium ion concentration, respectively, indicating risks for SIDS.

When calculating the amount of urea to be added to an infant formula or a pap in accordance with the present invention it has been found suitable according to the invention to start from the composition of the natural breast milk, in which case, however, the infant formula, like the natural breast milk, should contain a little less urea during the first weeks of life and later somewhat more.

As to the ammonium compound, the situation is somewhat more complex. Natural breast milk initially contains 400–500 µmol/l and this concentration decreases gradually. If, on the other hand, a defect intestinal flora of the neonate does not produce ammonium ion from urea, it would be natural to suppose that the content of ammonium ion should be equimolar to twice the natural concentration of urea. Furthermore, it is known that a grown-up person (and most likely also the little child) has an enterohepatic circulation of ammonium ion-urea. This mechanism allows a limitation to some extent (50–75%) of ammonium ion supplied perorally [Wheeler R A, et al, J Pediatr Surg, 26, 575–577 (1991)].

On basis of the considerations above an embodiment of the use according to the invention is characterized in that the ammonium compound and the urea, where appropriate, are added at a concentration of 0.2–0.6 mmol/l, preferably about 0.5 mmol/l, and at a concentration of 1–5 mmol/l, preferably about 2 mmol/l, respectively, to an infant formula ready and intended for administration to an infant during the first month of life.

Another embodiment of the use according to the invention is characterized on the same basis by adding the ammonium compound and the urea, where appropriate, at a concentration of 0.1–5 mmol/l, preferably 0.5–2 mmol/l, and at a concentration of 1–10 mmol/l, preferably 4–6 mmol/l, respectively, to an infant formula ready and intended for administration to a child during the months 2–7 of life.

In both these embodiments applies that if the child on diagnosing is found to lack urease-producing bacteria in its intestinal flora, an ammonium compound should primarily be added, in which case urea advantageously can be omitted, while supply of solely urea can occur when the child in its intestinal flora has bacteria of the type mentioned. The respective substance can in both cases be used in a concentration which is in the upper part of the ranges mentioned above. However, ammonia compound and urea can also be administered simultaneously, in which case the substances are used at a concentration which is in the lower part of the respective concentration range.

The infant formula or the pap according to the invention is intended to be given orally to the child in the form of a liquid but is preferably marketed in the form of a powder intended to be mixed with water as is conventional in case of infant formulas and paps.

It is fully possible per se to arrange the infant formula or pap according to the invention as a multiple component system in a kit which, for instance, comprises an infant formula or pap powder having a conventional composition and in one or more separate packages a physiologically innocuous ammonium compound and/or urea, said powder first being stirred into an appropriate amount for water and then the ammonium compound and/or the urea being stirred therein or the components being stirred into the water in reversed order.

Preferably, however, the ammonium compound and/or the urea is/are mixed with the other components of the infant formula or pap in connection with the manufacture thereof which can be performed by means of conventional methods, which usually result in a product in the form of a powder. In this case the amounts of ammonium compound and/or urea mixed into the product are adjusted in such a way that after the powder having been stirred into the intended amount of water a liquid product having the above stated concentrations of ammonium compound and urea, respectively, is obtained.

The ammonium compound to be used in accordance with the present invention is preferably ammonium chloride but also other physiologically innocuous ammonium compounds which have the required stability and solubility in water for the intended use are contemplated in this connection. When using ammonium chloride as an additive to conventional infant formulas or paps the contribution to the total content of chloride from other components therein should be taken into consideration so that the amount of ammonium chloride added is adjusted so that the total concentration of chloride ion in the finished infant formula/pap preferably is within the range of 10–15 mmol/l. Possibly, it may appear necessary to reduce the amount of any of the conventional chloride containing components of the infant formula/pap in order not exceed this level too much.

An infant formula or a pap which according to the invention has been added with a physiologically innocuous ammonium compound and/or urea in a physiologically innocuous and for the prevention of SIDS effective concentration is suitably administered to the child at every meal to prevent SIDS.

However, it is fully possible for prophylaxis of SIDS to administer a pharmaceutical preparation containing a physiologically innocuous ammonium compound and/or urea in a physiologically innocuous and for prophylaxis of SIDS effective concentration to the infant. This way of attaining prophylaxis of SIDS is especially of interest in case of children which are entirely supplied with the breast milk of the mother.

In order to investigate the risks for an infant to contract SIDS and to start on prophylactic treatment in time, all neonates, but especially premature and/or by caesarian section born children which are a special risk group, should as matter of routine be subjected to a control whether their faeces contain ammonium ions and urea and/or exhibit urease activity or not and the children which are found to lack this metabolite should be supplied with ammonium ion perorally.

For prophylaxis of SIDS it is also contemplated to administer to the gastrointestinal tract of the infant non-pathogenic, urease-producing bacteria which produce ammonium ions from the natural content of urea of the mother's milk or from urea added to the infant formula in a physiological amount. The provision that the bacteria should be non-pathogenic means in this connection that the bacteria culture has been selected and/or modified in such a way that it does not pose a hazard to the infant's health, i.e. the danger of infection and toxin to the child has been eliminated.

The invention will in the following be illustrated further by means of a number of working example which should not be construed as limiting the invention.

EXAMPLE 1

26.5 mg of ammonium chloride and 120 mg of urea are dissolved in 0.9 l of water while stirring. 130 g (about 0.3 l) of an infant formula/supplement to the mother's milk in powder form designed for infants from birth to 6 months, inclusive, (Findus Milkotal™ 1 from Svenska Nestlé AB, Bjuv, Sweden) are added to the solution while stirring to the formation of a homogenous dispersion. The product thus obtained constitutes an infant formula/supplement to the mother's milk intended for administration to an infant at the age of 0–6 months after appropriate tempering.

EXAMPLE 2

106 mg of ammonium chloride and 300 mg of urea are dissolved in 0.9 l of water while stirring. 130 g (about 0.3 l)

of an infant formula/supplement to the mother's milk in powder form designed for children from the age of 2 months (Findus Milkotal,™ 2 from Svenska Nestlé AB, Bjuv, Sweden) are added to the solution while stirring to a temperature of about 60° C. to the formation of a homogenous dispersion. The product thus obtained constitutes an infant formula/supplement to the mother's milk intended for administration to an infant at the age from 2 months after appropriate tempering. EXAMPLE 3

106 mg of ammonium chloride and 300 mg of urea are dissolved in 0.9 l of water while stirring. 140 g (about 0.4 l) of a base pap in powder form designed for children at the age of from 4 months (Findus basvälling™ from Svenska Nestlé AB, Bjuv, Sweden) are added to the solution while stirring and heating to about 45° C. to the formation of a homogenous dispersion. The product thus obtained constitutes a pap intended for administration to a child at the age from 4 months after appropriate tempering.

What is claimed is:

1. A composition for reducing the risk of sudden infant death syndrome (SIDS) in infants who have abnormally high intact urea concentration, abnormally low urease activity or abnormally low ammonium ion concentration in their feces, comprising an infant formula or pap and an effective amount of ammonium chloride as an additive to said infant formula or pap, wherein said effective amount of ammonium chloride is sufficient to reduce the risk of SIDS in infants who have abnormally high intact urea concentration, abnormally low urease activity or abnormally low ammonium ion concentration in their feces.

2. The composition of claim 1, wherein the ammonium chloride is present at a concentration of 0.2–0.6 mmol/l in said infant formula or pap.

3. The composition of claim 2, wherein the concentration of the ammonium chloride is 0.5 mmol/l.

4. The composition of claim 1, wherein the ammonium chloride is present at a concentration of 0.1–5 mmol/l.

5. The composition of claim 4, wherein the concentration of the ammonium chloride is 0.5–2 mmol/l.

6. The composition of claim 1, wherein said composition is in the form of a powder.

7. A method of reducing the risk of sudden infant death syndrome (SIDS) in infants who have abnormally high intact urea concentration, abnormally low urease activity or abnormally low ammonium ion concentration in their feces comprising:

(a) identifying an infant with abnormally high intact urea concentration or abnormally low urease activity in his or her feces, and administering a composition comprising an infant formula or pap and an effective amount of ammonium chloride as an additive to said infant formula or pap, wherein said effective amount of ammonium chloride is sufficient to reduce the risk of SIDS in infants who have abnormally high intact urea concentration or abnormally low urease activity in their feces; or (b) identifying an infant with abnormally low ammonium ion concentration but not abnormally high intact urea concentration or abnormally low urease activity in his or her feces, and administering a composition comprising an infant formula or pap and an effective amount of ammonium chloride, urea or mixture thereof, as an additive to said infant formula or pap, wherein said effective amount of ammonium chloride, urea or mixture thereof is sufficient to reduce the risk of SIDS in infants who have abnormally low ammonium ion concentration but not abnormally high intact urea concentration or abnormally low urease activity in their feces.

8. The method of claim 7, wherein the composition is administered to an infant during the first month of life, and the concentration of ammonium chloride in the composition is 0.2–0.6 mmol/l.

9. The method of claim 7, wherein the composition is administered to an infant during the during months 2–7 of life, and the concentration of ammonium chloride in the composition is 0.1–5 mmol/l.

10. The method of claim 7, wherein the composition is administered to an infant during the first month of life, and the concentration of urea in the composition is 1–5 mmol/l.

11. The method of claim 7, wherein the composition is administered to an infant during months 2–7 of life, and the concentration of urea in the composition is 1–10 mmol/l.

* * * * *